United States Patent [19]

Strimling

[11] Patent Number: 4,547,911
[45] Date of Patent: Oct. 22, 1985

[54] IMPLANTABLE HEART PUMP

[76] Inventor: Walter E. Strimling, 63 W. Cliff Rd., Weston, Mass. 02193

[21] Appl. No.: 557,592

[22] Filed: Dec. 2, 1983

[51] Int. Cl.⁴ .......................... A61F 1/24; A61M 1/03
[52] U.S. Cl. ...................................... 623/3; 417/412; 417/413; 417/418
[58] Field of Search ...................... 3/1.7, 1; 128/1 D; 417/413, 412, 418

[56]  References Cited
U.S. PATENT DOCUMENTS

| | | | |
|---|---|---|---|
| 3,434,162 | 3/1969 | Wolfe | 3/1.7 |
| 3,568,214 | 3/1971 | Goldschmied | 3/1.7 |
| 3,842,440 | 10/1974 | Karlson | 3/1.7 |
| 3,874,002 | 4/1975 | Kurpanek | 3/1.7 |
| 4,369,530 | 1/1983 | Robinson et al. | 3/1.7 |

Primary Examiner—Ronald L. Frinks
Attorney, Agent, or Firm—Bromberg, Sunstein & McGregor

[57]  ABSTRACT

A mechanical heart for implantation into the human body is run at a higher frequency which is a harmonic multiple of a normal heart beat frequency, and the pump chamber volume is reduced, proportionately to the increased pumping frequency. The circuit for controlling the frequency includes a phase locked loop for implementing a predictive algorithm which adjusts the frequency dynamically based on heart muscle nerve ending signals to synchronize the circuit output to the biologically determined heart beat. The reduced displacement permits use of a smaller compliance chamber. A novel interconnection between the motor chambers of a plurality of such pumps eliminates the need for venting and compliance chambers in a totally implanted heart system.

14 Claims, 3 Drawing Figures

IMPLANTABLE HEART PUMP

DESCRIPTION

Cross-Reference To Related Applications

My copending applications Ser. No. 257,752 filed Apr. 27, 1981 (now U.S. Pat. No. 4,468,177) and Ser. No. 347,184 filed Feb. 9, 1982 (now U.S. Pat. No. 4,512,726), respectively, disclose artificial heart devices which need no venting or external compressors and so are capable of being included within the body cavity even along with an internal power supply. But most potential artificial heart recipients are too small to provide a sufficiently large body cavity. Consequently, most must wait for the advent for more efficient heart pumps than are presently available.

This invention relates to implantable artificial heart devices and more particularly to such devices which may be included entirely within a chest cavity without the need for venting.

Background of the Invention

The successful implantation of an artificial heart in a human being is now history. It is also well known that a candidate for such an operation, among other requirements, had to be of considerable size to provide a sufficiently large body cavity to receive an artificial heart of the size necessary to pump the requisite volume of blood. It has also been well publicized that exit tubes from the body were required for proper venting and for an external compressor connection.

Brief Description of the Invention

A heart pump according to the present invention is driven at a frequency which is high compared to the familiar heart impulse rate, and is synchronized thereto. The pump stroke frequency is n/m times the normal heart beat rate, where n is an integer greater than m, and m is a small integer but greater than 1. In the classical case, n/m=1 is the normal heart beat frequency. This multiple n/m is referred to below and in the claims by "N". It is a low denominator fractional multiple, which may be, e.g., 1½, 2, 2½ or more. For ease of synchronization with the normal heart beat, a convenient pump frequency is approximately two hundred and sixteen beats per minute, or 3×72 (where 72 is the normal heart beat).

The frequency of the pump is limited by acceptable pressure gradients and by the possibility of blood cell damage. Nevertheless, relatively high pump rates are acceptable; this permits a given net flow of blood to be achieved with a pump which is proportionately reduced in weight and size. Increased motor efficiency is achieved at the relatively higher speed of rotation. In a preferred mode of operation of the invention a plurality of such small higher frequency pumps are driven in opposing pumping phases and their motor chambers connected to a common conduit, eliminating venting requirements. A compliance chamber may be connected to the conduits to further reduce pressure variations.

The operation of a heart pump at a frequency high compared to the normal heart frequency to reduce the size of a heart pump, and the use of two pumps, synchronized to provide an unvented heart pump system, are considered significant departures from prior art thinking.

Detailed Description

Figure 1:
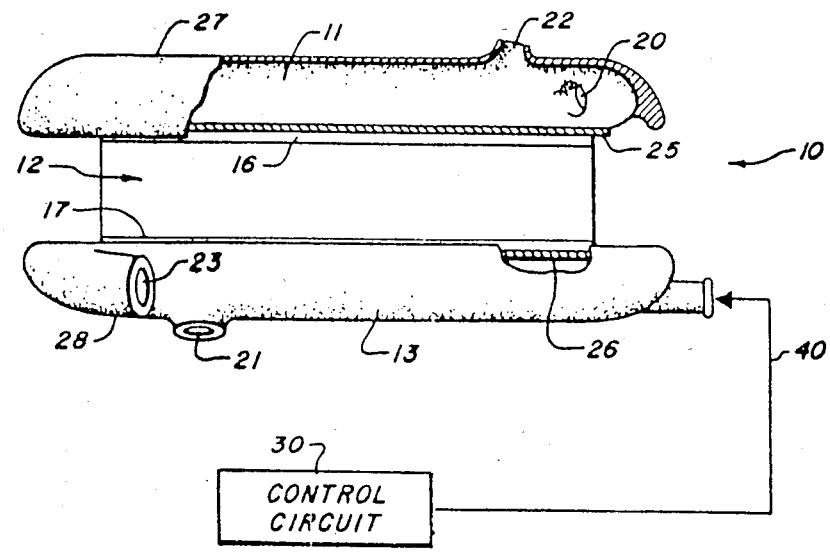
FIG. 1 is a side view, partially cut away, of a pump useful as a heart implant.

FIG. 1 shows a side view of a prior art pump 10 suitable for implantation into a human body in accordance with an embodiment of this invention. The pump is disclosed in detail along with its operation in my copending application Ser. No. 347,184 filed Feb. 9, 1982.

The pump includes three chambers 11, 12, and 13, a motor being housed in the central chamber 12. The motor comprises a stator and a rotor, not shown, which causes a rotary motion of the rotor when the stator is activated. The rotary motion is translated into an up and down motion of two pusher plates 16 and 17 by a wheel and ramp mechanism, also not shown but fully described in my above-mentioned copending application. All that is important for an understanding of the present invention is that pusher plates 16 and 17 move up and down respectively as viewed in a push-pull fashion to reduce the volumes of chambers 11 and 13 alternatively. In this manner blood enters chambers 11 and 13 by means of inlets 20 and 21 and exits the chambers by outlets 22 and 23 respectively.

Most notable, the total volume of the three chambers is constant, as is the volume of the central motor chamber. Consequently, there is no need to vent to the exterior of the body. The chambers are sealed by diaphragms 25 and 26 which are attached to the rim of cover plates 27 and 28 thus forming flexible sealing walls of the chambers against which pusher plates 16 and 17 press. In the pump shown in FIG. 1, the parallel arrangement of pusher plates 16 and 17 is such that chamber 11 expands when pusher plates 16 and 17 are lowered and chamber 13 contracts. Chamber 12, housing the motor and plate-driving mechanism, retains a constant volume but is displaced downward since its walls (the pusher plates) are displaced downward in parallel.

The size of a heart implant is determined by the amount of blood required by the body. Each beat of a normal heart pumps eighty-three milliliters of blood. An average heart beats about seventy-two times per minute. Consequently, about six liters of blood are pumped per minute by a normal heart. Existing approaches to artificial heart design have attempted to match these figures. However a pump with an 83 ml net displacement is rather bulky and thus is suitable for a limited number of persons.

Furthermore, in existing pumps, the displacement of an 83 ml volume via a piston or membrane-type element, necessarily implies a corresponding 83 ml displacement swept out by the opposing surface of the piston or membrane which defines a wall of the motor drive chamber. If the motor drive chamber were sealed, the piston (or membrane) would have to perform work in moving back and forth against the pressure gradient in the chamber, thus reducing the efficiency of the motor as a blood pump. To overcome this problem, current experimentation in implantable hearts relies upon vents for the drive chamber which open to the atmosphere; or relies upon the use of "compliance chambers". (A compliance chamber is a chamber in fluid communication with the drive motor chamber and having at least one large flexible wall. The wall displaces slightly to accommodate variations in pressure in the drive chamber induced by the normal pumping motions The slight movements of the wall reduce the fluid pressure differential, or back pressure, hence reduce the total auxiliary energy drain otherwise resulting from pump motion).

In accordance with the present invention the size of the pump is reduced by increasing the frequency of the pump by a factor of n/m, ($n > m \geq 1$), and utilizing a chamber of proportionately reduced volume, so as to pump an equivalent volume of blood per unit time. A smaller compliance chamber may thus be used.

A proposed theory for increasing the frequency of the pump by some low denominator fractional multiple of a normal heart frequency of seventy-two beats per minute will now be explained.

The frequency at which the pump operates is determined by control circuit 30. Control circuit 30 is responsive to pulses from nerve endings in the heart muscle of the human body. The circuit includes an EMG (Electromyograph) transducer, an amplifier and a processor which can be exactly the same as employed in commercial pacemakers, and which can include circuitry which is standard in commercial pacemakers to generate signals that simulate the rhythm of the heart signals, in the event that such heart signals do not occur at appropriate intervals. Such apparatus is represented by block 31 in FIG. 2. The apparatus outputs an appropriate electrical signal 32 synchronized to a heart beat detected by the EMG. This output is applied to a frequency multiplier circuit comprising a phase-locked loop circuit which implements a predictive algorithm for generating the high frequency pulses required. The circuit for implementing the predictive algorithm is represented by block 35 in FIG. 2. The frequency multiplier also includes a divide by (n/m) circuit.

Now we will turn our attention to the predictive algorithm and examine some of the considerations which dictate the form of that algorithm.

Every particle of matter appears to have a characteristic pattern of timed repetition of motion. The human body has its pattern also. Most clearly, one part of the human pattern is the beating of the heart.

Consciousness exists at many levels. The differentiation between levels is most obvious when observing some of the functions of the brain. But all of the body has its processes, not just the brain. At some level, somewhere or everywhere, the body is a clock, measuring time and signaling the heart muscle to contract and pump blood. The timing and amount of contraction are fully controlled, but the knowledge of that control is not at the forefront of our consciousness.

When a heart is transplanted from another person, the host body recognizes and attempts to take control of the foreign heart. In a successful transplant, beating is synchronized with and controlled by the body's clock. The timing and amount of contraction are fully controlled within the limitations of the new heart's strength and ability to comply.

When any mechanical heart or heart assist device is installed in a human body's blood circulation system, the rhythm of the mechanical heart or heart assist device, and the flow characteristics from the device should be responsive to the appropriate body control signals. If the mechanical heart or heart assist device does not respond appropriately to the body signals of time, intensity or quantity, the body's heart control center or centers are frustrated. The frustration at this subconscious level can become overwhelming in its intensity.

Just as total, unending frustration at the level of full consciousness can result in consciously controlled violence, similar frustration at a level of the subconscious can result in subconsciously controlled violence which may manifest itself, for example, in convulsions.

Convulsions do occur, of course, without the installation of a mechanical heart. Perhaps among other times, they may occur whenever major body control centers are frustrated in their many and varied endeavors. One way to avoid convulsions would be to make sure that the body control centers are able to exercise their normal control functions and that these body control centers receive timely responses that indicate to them that their control signals have been sent, have been received, and have been acted upon appropriately. This does not mean that a mechanical heart or heart assist device must emulate in all respects the function of a human heart. What it does mean is that one must be consciously aware that the subconscious is aware, and that it must not be ignored except at great risk.

One way to assist the body control centers in exercising control over the normal body functions is to harmonize the pumping of an implanted heart to the natural heart parameters, by making it pump at a frequency which is a harmonic multiple of the normal frequency, and reducing the pump volume to preserve the normal flow rate. This may be accomplished, for example, by increasing the pumping frequency of the pump to some half-integral multiple of the normal heart frequency. For example, if the frequency were doubled to one hundred and forty-four beats per minute, the displacement volume of the chambers in FIG. 1 would need be only one-half the size that it would otherwise have to be to pump the requisite volume of blood. In this doubled frequency case, and generally for any integral harmonic pump frequency, the body control centers will still receive a pump signal at those times corresponding to a normal heart signal, and the normal bodily control processes will not be frustrated. (It bears noting that to the extent various bodily processes, such as ion transport across membranes, may depend upon the occurrence of periodic fluid pressure pulses, such basic physicodynamic requirements will also be closely approximated by the harmonic frequency pumping of the present invention.)

Figure 2:
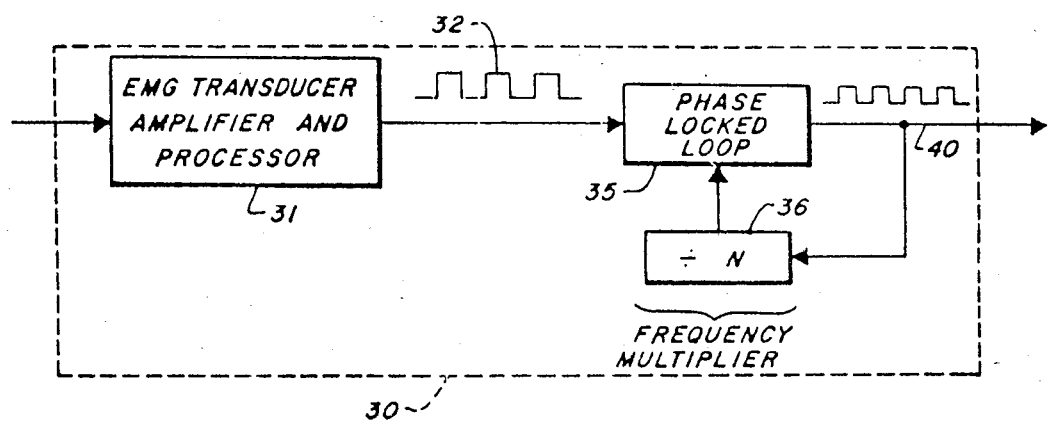
FIG. 2 is a block diagram of a circuit for operating a pump of the type shown in FIG. 1, of reduced size, at an elevated frequency, in accordance with this invention.

The circuit of FIG. 2 is adapted to respond to an input signal from a heart muscle nerve ending, indicating when a normal heart would beat. The circuit then provides a higher frequency pulse to the artificial heart, at a frequency which, as in the above example may be a half-integral multiple of the frequency of the input signal and which is synchronized to the input signal. The body control centers thus not only receive pump signals seventy-two times per minute but also, those signals occur when normal heart signals would be present.

More generally, the harmonic multiple $N = n/m$ of the normal heartbeat should have the property that a significant number of the pump strokes occur at the times when a normal heartbeat would occur. In the example above, where N is 2, every other pump stroke occurs at a normal heartbeat time, and in fact each normal heartbeat has one simultaneous corresponding pump stroke (as well as one intermediate pump stroke). More generally, for N of the form n/m (n, m integers with n>m and m≧1) a pump stroke will coincide with every mth heartbeat. In addition, if m and n have a common divisor (i.e. n=cn', and m=cm', where n', m' are integers less than n and m respectively) then there will also be intermediate heartbeats before the mth heartbeat when the pump stroke and the normal heartbeat coincide. The number N is referred to a harmonic multiple of the heartbeat. One sense in which the pump frequency is tuned to the normal heart is that a significant number of pump strokes occur at the times a normal heartbeat occurs, thus reinforcing the natural rhythm of the body. The larger the denominator m, the smaller the proportion of normal heartbeats that are matched, and accordingly as m increases above, say, 5 or 6 it is expected that the beneficial results of the invention would not be realized to as great an extent and a pump so operated would be roughly analogous to a continuous flow pump. Accordingly, the term harmonic multiple as used below and in the claims refers to a multiple which is a low denominational fractional multiple of the normal heart beat.

It is important also to be able to vary the flow of blood. The predictive algorithm contains provisions to "differentiate" or determine the rate of change in the EMG over periods of time, and to correspondingly decrease or increase the pump frequency in proportion to a decreasing or increasing normal heart frequency. In this manner, the body control centers receive feedback signals consistent with normal signals.

It is important also that blood pressure remain within normal limits between about 150 mm Hg (diastole) and 100 mm Hg (systole) with a mean pressure of about 120 mm Hg. The inclusion of pressure transducers such as a Koningsberg transducer in heart implants for monitoring pressure is well understood in the art, and the circuitry may or may not incorporate means responsive to the sensed blood pressure for changing the pump efficiency or duty ratio.

Within normal pressure constraints, the frequency of the beat signal supplied to an artificial heart in accordance with this invention can be increased to three, four or even more times the normal heart beat. Each such increase reduces the requisite size for the pump volume. The actual volume for the chambers of the implant can be determined by the following equation:

$$\frac{\text{Chamber volume of mechanical heart}}{\text{Chamber volume of the natural heart}} = \frac{K \text{ (Normal pulse rate)}}{\text{Mechanical heart rate}}$$

where K is a constant relating to friction, pressure and the geometry of the pump chambers, and is determined by empirical and mathematical analysis of the hydraulics of the particular pump, as is well understood. The chamber volume of a presently available mechanical heart is about 80 to 90 milliliters.

The pump of the illustrative arrangement of FIG. 1 is driven by a sequence of pulses applied to a plurality of specially distributed electrical conductors attached to a stator in the motor housed in chamber 12. The operation and drive circuit for providing activating pulses to the stator for driving the rotor are fully disclosed in my above-mentioned copending application. It is important to understand that the high frequency pulses supplied by control circuit 30 are applied to the stator along conductor 40 of FIGS. 1 and 2. Each such pulse initiates a stator pulse sequence for one rotation of the rotor exactly as each relatively low frequency pulse did, as disclosed in my above mentioned copending application.

The pump arrangement of FIG. 1 includes appropriate check valves for permitting blood flow only in desired directions. A full discussion of such valves is included in my aforementioned patent applications.

It will be appreciated that the present invention of an implanted heart which is synchronized to a half-integral multiple of a normal heart beat not only maintains the biological rhythm of a normal heart but results in a smaller pump which is more readily implantable in a greater proportion of would-be recipients than presently available pumps. While preferred embodiment of invention has been shown and described in respect of a two-chamber pump, with the two chambers alternately expanded and contracted so that the volume of the motor/drive housing remains constant, the smaller pump size achieved by the invention allows other single and multiple-pump configurations.

Figure 3:
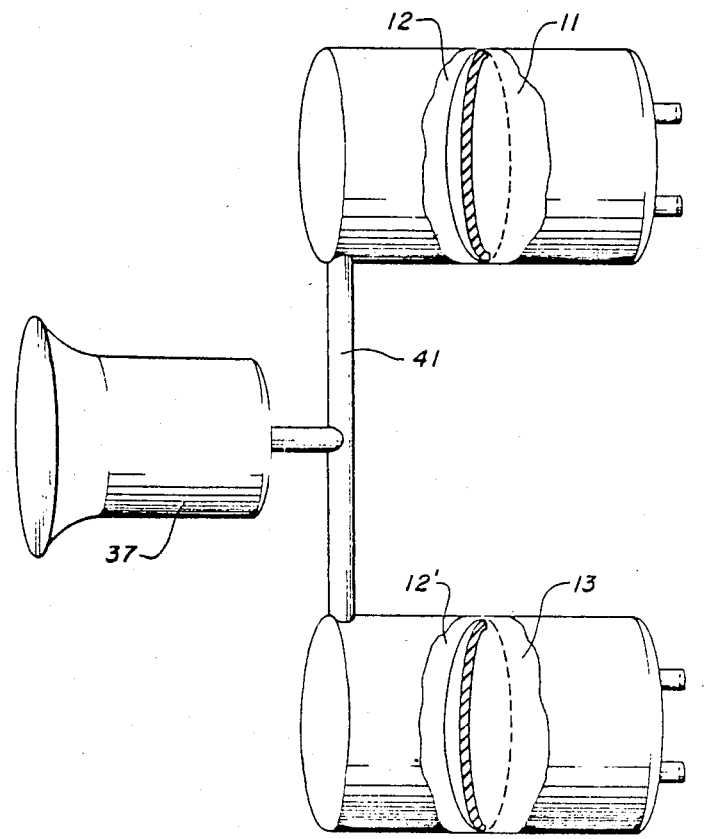
FIG. 3 is a pump system, including compliance chamber, utilizing multiple pumps according to the present invention.

Thus, the invention can be practiced with two pumps each identical to a portion of the pump of FIG. 1. Such an arrangement is shown in FIG. 3. Two pumps, one comprising only chamber 11 along with a motor chamber such as 12; the other comprising only chamber 13 along with a motor chamber 12' can be implanted in two body cavities of relatively small size. For example, one such pump could be placed in the region vacated by a human heart; the other could be located in a space below the diaphragm. The compression cycle of one pump chamber is synchronized with the expansion cycle of the other pump chamber and the motor chambers are connected by a flexible conduit 41 which permits fluid to flow therebetween. Since the pumps are operated in opposing phases, the changes in motor chamber volume are substantially equal and opposite so that there is a minimal net change in total volume of the two motor chambers during operation. Thus there is no need to vent to the exterior of the body. Each such pump benefits from the size reduction achieved by its relatively high frequency operation. Such a spaced-apart pump system may be further benefited by connecting a compliance chamber 37 to the flexible conduit 41 between pumps. The connection to the compliance chamber is a flexible fluid conduit which allows the compliance chamber to receive and expel fluid as required. In this manner, any net negative pressure which is developed in the pump motor chambers is controlled to a minimum to avoid potential arterial collapse. Because of the small total displacement of the pumps, a smaller compliance chamber may be effectively employed.

It will be clear that using the harmonically tuned space reducing pump system of the present invention, the motor chambers may also be interconnected in systems of more than 2 pumps, preferably driven in a phased relationship so that the net change in volume of the chambers is close to zero. Also, the invention can be practiced with a single pump, used for example, as a left ventricular assist device. The higher frequency operation permits a reduction in size for the single pump, and by reducing the displacement volume of fluid on the non-blood side of the piston or diaphragm, permits total implantation with a smaller compliance chamber than would otherwise be required. The higher frequency operation can result in increased efficiency for both the pump and the compliance chamber in this embodiment. Accordingly the claims are intended to cover all such variations of the invention.

What is claimed is:

1. A mechanical heart pump for implantation into a human body, said pump comprising:

first and second chambers, the first chamber having inlet and outlet conduits;

first movable element separating the first and second chambers;

drive means, at least a portion of which is disposed in the second chamber, for driving the first movable member so as to alternately expand and reduce the volume of the first chamber; and control means, responsive to each of a sequence of body signals representing heart beats at a frequency f, for actuating the drive means at a second frequency Nf where N is a harmonic multiple greater than one.

2. A mechanical heart pump in accordance with claim 1, further including a third chamber having inlet and outlet conduits; and a second movable element separating said second and third chambers, and driven by the drive means;

wherein the drive means further includes synchronizing means for alternately reducing and expanding the volume of said third chamber in a manner synchronized with the expansion and reduction of the volume of said first chamber respectively, so that the first movable element reduces the volume of the second chamber as the second movable element expands the volume of the second chamber and the volume of the second chamber remains substantially constant 3. A mechanical heart pump in accordance with claim 2 wherein N is n/2, n being an integer equal to 3 or more.

4. A mechanical heart pump in accordance with claim 3 wherein said control means includes:

means for detecting a signal from a heart muscle nerve ending;

means connected thereto for providing a synchronizing signal; and frequency multiplier means responsive to said synchronizing signal for actuating the drive means N times.

5. A mechanical heart pump in accordance with claim 1 in which said inlet and outlet conduits of the first chamber are adapted and sized for connection to a vein and an artery of a first blood circulating system.

6. A mechanical heart pump in accordance with claim 2 in which the inlet and outlet conduits of the first chamber are adapted and sized for connection to a vein and artery of a first blood circulating system and the inlet and outlet conduits of the third chamber are adapted and sized for connection to a vein and artery of a first blood circulating system.

7. An implantable heart pump according to claim 1, further including:

third and fourth chambers, the third chamber having inlet and outlet conduits;

a second movable element, separating said third and fourth chambers;

second drive means, at least a portion of which is disposed in the fourth chamber, for driving the second movable member so as to alternately expand and reduce the volume of the third chamber;

wherein the control means further includes means for controlling the first and second drive means in a manner to synchronize the expansion and reduction of volume of the third chamber with the reduction and expansion respectively of the first chamber; and wherein the second and fourth chambers are connected in a closed fluid circuit so that changes in volume of the second chamber caused by motion of the first movable element are approximately opposite to changes in volume of the fourth chamber caused by motion of the second movable element, so that the total change in net volume of the second and fourth chambers is substantially zero.

8. A heart pump system according to claim 7, further including a compliance chamber connected in the closed fluid circuit of the second and fourth chambers.

9. An improved artificial heart system including a pump for implantation into the human body, of the type having inlet and outlet conduits, and operative to execute an inlet or suction stroke, and an outlet or pumping stroke, such strokes together comprising a pump cycle, wherein the improvement comprises:

control means, in communication with the pump, for causing the pump to execute pump cycles at a frequency Nf which is a harmonic multiple N, where N is greater than one, of the normal hearbeat f.

10. An artificial heart according to claim 9 wherein the control means further includes:

first means for sensing the normal heart beat signals at a heart muscle nerve; and multiplier means connected to the first means for generating in response to each said normal signal, signals for causing the pump to execute N pump cycles.

11. An artificial heart system according to claim 9, including a plurality of pumps, wherein the control means includes means for causing each pump to execute pump cycles at the frequency which is N times the normal heart beat.

12. An artificial heart system according to claim 11, wherein the total displacement of the plurality of pumps is approximately equal to 1/N times the normal heart displacement.

13. An artificial heart system according to claim 11, wherein each pump includes a fluid pumping chamber and a non-pumping chamber, each said non-pumping chamber undergoing an instantaneous change in volume oppositely related to the instantaneous change in volume of the corresponding fluid pumping chamber, and wherein the non-pumping chambers of all the pumps are connected in fluid communication with each other thereby defining a non-pumping volume larger than that of each pump.

14. An artificial heart system according to claim 13 wherein the control means further includes means for causing the pumps to execute their pump cycles out of phase with each other in a manner so that the net instantaneous change in volume of the larger non-pumping volume is substantially zero.

* * * * *